United States Patent
Kounaves et al.

(10) Patent No.: US 6,527,930 B1
(45) Date of Patent: Mar. 4, 2003

(54) MICROFABRICATED ARRAY OF IRIDIUM MICRODISKS

(75) Inventors: Samuel P. Kounaves, Winchester, MA (US); Melissa A. Nolan, Henderson, NV (US)

(73) Assignee: Trustees of Tufts College, Medford, MA (US)

( * ) Notice: Subject to any disclaimer, the term of this patent is extended or adjusted under 35 U.S.C. 154(b) by 0 days.

(21) Appl. No.: 09/598,115

(22) Filed: Jun. 21, 2000

Related U.S. Application Data

(60) Provisional application No. 60/142,234, filed on Jul. 2, 1999.

(51) Int. Cl.[7] .............................................. G01N 27/42
(52) U.S. Cl. ..................... 204/434; 204/412; 204/413
(58) Field of Search ............................... 204/434, 403, 204/412, 413

(56) References Cited

U.S. PATENT DOCUMENTS

| | | | |
|---|---|---|---|
| 5,174,883 A | 12/1992 | Martin et al. | |
| 5,378,343 A | 1/1995 | Kounaves et al. | 204/413 |
| 5,431,800 A | 7/1995 | Kirchhoff et al. | |
| 5,865,972 A * | 2/1999 | Buffle et al. | 204/412 |

OTHER PUBLICATIONS

Gillespie et al "Chemistry", p. 311, 1986, month N/A.*

Agraz, R., et al., "Chemically Modified Electrode for the Simultaneous Determination of Trace Metals and Specification Analysis," *Analytica Chimica Acta*, vol. 273; 205–212 (1993).

Baldo, M., et al., "Lead and Copper Deposition from Dilute Solutions onto Carbon Disc Microelectrodes. Assessment of Quantification Procedures by Anodic Stripping Voltammetry," *Electrochimica Acta*, vol. 43, No. 23; 3413–3422 (1998).

Belmont, C., et al., "Mercury–plated iridium–based microelectrode arrays for trace metals detection by voltammetry: optimum conditions and reliability," *Analytica Chimica Acta*, vol. 329; 203–214 (1996).

Brzezinska, M.B., et al., "Application of Anodic Stripping Voltammetry with Thin Mercury–Film Electrodes in Analysis of Natural Water," *Chem. Anal.*, vol. 38; 527–534 (1993).

Cai, K., et al., "Voltammetric Determination of Trace Amounts of Mercury with a Carbon Paste Electrode Modified with an Anion–Exchanger," *Fresenius, J. Anal. Chem.*, 345; 25–31 (1993).

Fakhari, A.R., et al., "PVC–Based Hexathia–18–Corwn–6–Tetraone Sensor for Mercury (II) Ions," *Anal. Chem.*, vol. 69, No. 18; 3693–3696 (Sep. 15, 1997).

Feeney, R., et al., "Analytical Characterization of Microlithographically Fabricated Iridium–Based Ultramicroelectrode Arrays," *Electroanalysis*, vol. 10, No. 2; 89–93 (1998).

Gil, E.P., et al., "Potentiometric Stripping Determination of Mercury (II), Selenium (IV), Copper (II) and Lead (II) at a Gold Film Electrode in Water Samples," *Analytica Chimica Acta.*, vol. 293; 55–65 (1994).

(List continued on next page.)

*Primary Examiner*—Robert J. Warden, Sr.
*Assistant Examiner*—Kaj K. Olsen
(74) *Attorney, Agent, or Firm*—Nutter, McClennen & Fish LLP

(57) ABSTRACT

An ultramicroelectrode is disclosed which includes a) a silicon substrate; b) a silicon oxide insulating layer; c) a titanium adhesion layer; d) an iridium layer; e) a gold bond pad layer; f) a titanium adhesion layer; and g) a silicon dioxide insulating layer. In a preferred embodiment, the f) and g) layers have been partially or totally removed. Preferably, the ultramicroelectrode of the invention does not include mercury.

19 Claims, 5 Drawing Sheets

OTHER PUBLICATIONS

Gustavsson, I., "Detrmination of Mercury in Sea Water by Stripping Voltammetry," *J. Electroanal. Chem.,* vol. 214; 31–36 (1986).

Hatle, M., "Determination of Mercury by Differential–Pulse Anodic–Stripping Voltammetry with Various Working Electrodes," *Talanta,* vol. 34, No. 12; 1001–1007 (1987).

Herdan, J., et al., Field Evaluation of an Electrochemical Probe for in Situ Screening of Heavy Metals in Groundwater, *Environ. Sci. Technol.,* vol. 32; 131–136 (1998).

Jaya, S., et al., "Simplified Anodic–Stripping Voltammetric Determination of Mercury in Sea Water Using a Glassy Electrode and an Acetate–Chloride Buffer," *Analyst,* vol. 110; 1361–1364 (Nov. 1985).

Jeong, E.D., et al., "Simultaneous Determination of Lead, Copper, and Mercury at a Modified Carbon Paste Electrode Containing Humic Acid," *Electroanalysis* vol.6; 887–893 (1994).

Kim, H.J., et al., "Determination of $Hg^{II}$ Ion with a 1, 11–Bis(8–quinoyloxy)–3, 6, 9–Spin–Coating Tecnique," *Electroanalysis,* vol. 10, No. 5; 303–306 (1998).

Kounaves, S., et al., "Iridium–Based Ultramicroelectrode Array Fabricated by Microlithography," *Anal. Chem.,* vol. 66, No. 3; 418–423 (Feb. 1, 1994).

Rievaj, M., et al., "Application of Gold Fiber Voltammetric Microelectrode in Trace Analysis of Mercury in Waters and Fertilizers," *Anales de Quimica,* 347–350 (1993).

Rievaj, M., et al., "Determination of Mercury and Copper Traces in Ultrapure Spectral Carbon by DPASV on a Gold–Fibre Microelectrode," *Collect. Czech. Chem. Commun.,* vol. 58; 2918–2923 (1993).

Sipos, L., et al., "New Voltammetric Procedure for the Simultaneous Determination of Copper and Mercury in Environmental Samples," *Fresenius Z. Anal. Chem.,* vol. 298; 1–8 (1979).

Sousa, M., et al., "Preconcentration and Voltammetric Determination of Mercury (II) at a Checmically Modified Glassy Carbon Electrode," *Anal. Chem.,* vol. 68; 1258–1261 (1996).

Tercier, M.L., et al., "In Situ Voltammetric Measurement of Trace Elements in Lakes and Oceans," *Analytica Chimica Acta.,* vol. 237; 429–437 (1990).

Ugo, P., et al., "Ion–Exchange Voltammetry of Trace Mercury (II) at Glassy Carbon Electrodes Coated with a Cationic Polypyrrole Derivative. Application to Pore–Waters Analysis," *Electroanalysis,* vol. 9, No. 15; 1153–1158 (1997).

Ugo, P., et al., "Voltammetric Determination of Trace Mercury in Chloride Media at Glassy Carbon Electrodes Modified with Polycationic Ionomers," *Analytica Chimica Acta,* vol. 305; 74–82 (1995).

Uhlig, a., et al., "Highly Sensitive Heavy Metal Analysis on Platinum–and Gold–Ultramicroelectrode Arrays," *Electroanalysis,* vol. 9, No. 2; 125–129 (1997).

Viltchinskaia, E.A., et al., "Simultaneous Determination of Mercury and Arsenic by Anodic Stripping Voltammetry," *Electroanalysis,* vol. 9, No. 8; 633–640 (1997).

Wang, E., et al., "Potentiometric Stripping Analysis with a Thin–Film Gold Electrode for Determination of Copper, Bismuth, Antimony and Lead," *Anal. Chem.,* vol. 56; 1903–1906 (1984).

Wang, F., et al., "Application of Differential Pulse Anodic Strippling Voltammetry with a Stopped–Flow System for the Simultaneous Determination of Pb, Cu, Sb and Bi in Environmental Samples," *Anal. Letters,* vol. 27, No. 9; 1779–1787 (1994).

Wang, J., "Remote Electrochemical Sensor for Monitoring Trace Mercury," *Electroanal.,* vol. 10, No. 6; 399–402 (1998).

Williams, G., et al., "Field–Based Heavy Metal Analyser for the Simultaneous Determination of Multiple cations On–Site," *Analyst,* vol. 119; 2337–2341 (Nov. 1994).

Zen, J.M., et al., "Square–Wave Voltammetric Striping Analysis of Mercury (II) at a Poly(4–vinlypyridine)/Gold Film Electrode," *Anal. Chem.,* vol. 67; 3571–3577 (1995).

* cited by examiner

MICROFABRICATED ARRAY OF IRIDIUM MICRODISKS

This application claims priority to Provisional Application No. 60/142,234, filed on Jul. 2, 1999, the contents which are incorporated herein in their entirety.

STATEMENT REGARDING FEDERALLY SPONSORED RESEARCH

This work was supported in part by grants from the Environmental Protection Agency through the Northeast Hazardous Substance Research Center at NJIT (R-67), and the National Science Foundation (CHE-9256871). The government may have certain rights in the invention.

FIELD OF THE INVENTION

The technical field of this invention is microelectrodes and, in particular, methods and devices which employ iridium microdisks capable of determining Cu2+ or Hg2+ using square wave anodic stripping voltammetry.

BACKGROUND OF THE INVENTION

Determination at ppb levels of Cu2+ and Hg2+ is of special concern in both environmental and process monitoring. Copper is an essential element to the human diet, but intake of large quantities can be toxic. Soluble copper compounds in drinking water pose the greatest threat to humans. The average concentration of copper in tap water ranges from 20 to 75 ppb although many drinking water sources are higher due to the use of copper pipes and brass faucets. Being able to monitor and control the concentration of Cu2+ is also becoming important in the microelectronics fabrication industry, especially in very corrosive or harsh chemical conditions. On the other hand, mercury, even at low concentrations is one of the most toxic metals in the environment. Thus, the development of simple, reliable, and low-cost techniques for the determination of these metals is essential.

A variety of electrode substrates have been used for the determination of Cu2+. These have included; a mercury plated iridium microelectrode array (Jr-UMEA),[1-4] a thin film gold electrode,[5] a carbon disc microelectrode,[6] a hanging mercury drop electrode,[7] a mercury film electrode,[8] and a mercury plated platinum microelectrode array.[9] On-site analysis of copper has been performed using a mercury film glassy carbon electrode.[10] In situ analysis of copper has also been performed with a mercury drop electrode,[11] a mercury plated Ir-UMEA,1 and an agarose-coated mercury plated Ir-UMEA.3 The determination of Hg2+ has been achieved mainly with two types of electrodes, modified electrodes [12-18] and solid electrodes, such as carbon [19,20] and gold. [19,21-24] Determination of copper with simultaneous deposition of mercury has been performed using chemically modified [25, 26] and gold electrodes. [27-29]

For anodic stripping voltammetry (ASV), mercury is still widely used because of its large hydrogen overpotential, uniform surface, and suppression of underpotential peaks. However in many cases, such as measurements in environmental samples, in-vivo, in corrosive solutions, or where mercury plating is not feasible, mercury coated electrodes are practical. On the other hand, the direct use of solid substrates such as glassy carbon, Au, and Pt, has always been problematic because the stripping voltammograms display multiple peaks and distorted signals, making analysis difficult. The microfabricated iridium ultramicroelectrode (Ir-UME), coated with a mercury film, has been widely used for stripping voltammetric analysis of Cu2+ and several other heavy metals. [1-4] Even though bare iridium has a small potential window between hydrogen evolution and iridium oxidation, metals whose redox potential falls between these limits, such as Cu and Hg, may lend themselves to such an analysis.

SUMMARY OF THE INVENTION

The present invention is based, at least in part, on a discovery involving characterization and separate electrochemical determinations of Cu2+ and Hg2+ directly on a microlithographically fabricated array of iridium ultramicroelectrodes (Ir-UMEA), Square wave anodic stripping voltammetry was used to optimize experimental parameters such as supporting electrolyte, square wave frequency, and deposition time and potential. Reproducible stripping peaks were obtained for solutions containing low parts-per-billion (ppb) concentrations of either metal. It was discovered that excellent linearity was obtained for Cu2+ in the 20–100 ppb range and for Hg2+ in the 1–10 ppb range when using the bare iridium substrate. Detection limits were calculated to be 1 ppb (0.1 M KNO3 and 0.1 M HClO4, deposition time 180 s) and 5 ppb (0.1 M H2SO4, deposition time 120 s) for Cu2+ (S/N=3) and 85 ppt for Hg2+ (deposition time 600s). The experimental detection limits were determined to be 5 ppb for Cu2+ (deposition time 180 s) and 100 ppt for Hg2+ (deposition time 600s). Interference studies were performed and it was determined that Pb, Zn, and Cd had little or no influence on the copper signal. Tap water and spring water samples were analyzed for copper and good agreement was obtained with conventional methods. An unexplained effect of chloride ions on the iridium surface was noted. Further investigation by atomic force microscopy determined that changes on the surface occurred but could be eliminated when chloride leakage from the reference electrode is minimized. The solid state construction of the Ir-UMEA makes it a prime candidate for use in determining of Cu(II) and Hg(II) in chemically harsh environments.

In one aspect of the invention, an ultramicroelectrode includes: a) a metallic substrate; b) a first metallic oxide insulating layer; c) a first metallic adhesion layer; d) an iridium layer; e) a metallic bond pad layer; f) a second metallic adhesion layer; and g) a second metallic oxide insulating layer. The metallic substrate can be carbon, silicon, aluminum, phosphorous, gallium, indium, tin, antimony, selenium or germanium based., preferably silicon based. The first metallic oxide insulating layer can be a Group IV metallic oxide such as a Si, Ge, or Sn oxide, preferably a Si oxide. Typically the first metallic adhesion layer is a transition metal such as Ti, V, Cr, Sc, Nb, Mo, W, or, preferably Ti. The ultramicroelectrode also includes a metallic bond pad layer which can be Ni, Zn, Pd, Ag, Cd, Pt, Ga, In, or Au, preferably Au. The second metallic adhesion layer can be a transition metal such as Ti, V, Cr, Sc, Nb, Mo, W, or Ta, preferably Ti. The second metallic oxide insulating layer can be a Group IV metallic oxide such as Si, Ge, or Sn, preferably a silicone oxide. In preferred embodiment, the ultramicroelectrode of the invention does not include a mercury layer.

In certain aspects of the invention, one or more of the layers can be omitted from the ultramicroelectrode. The layers which can be eliminated can be determined by those skilled in the art and can include the omission of the first metallic oxide insulating layer and/or a second metallic adhesion layer and/or a second metallic oxide insulating layer; a first metallic adhesion layer and/or a second metallic adhesion layer and/or a second metallic oxide insulating layer; and a second metallic adhesion layer and/or a second metallic oxide insulating layer.

In a preferred embodiment, the ultramicroelectrode of the invention includes a) a silicon substrate; b) a silicon oxide insulating layer; c) a titanium adhesion layer; d) an iridium layer; e) a gold bond pad layer; f) a titanium adhesion layer; and g) a silicon dioxide insulating layer. In a preferred embodiment, the f) and g) layers have been partially or totally removed.

In still another embodiment, the present invention includes methods for producing an ultramicroelectrode by thermally growing a first metallic oxide insulating layer onto a metallic substrate followed by evaporating a first metallic adhesion layer onto the first metallic oxide layer. An iridium layer is the deposited onto the first metallic layer and a metallic bond pad layer is deposited onto the iridium layer. A second metallic adhesion layer is evaporated onto the metallic bon d pad layer and a second metallic oxide insulating layer is then deposited onto the second metallic adhesion layer. Preferentially, a portion or all of the second metallic adhesion layer and second metallic oxide insulating layer is removed.

BRIEF DESCRIPTION OF THE DRAWINGS

The invention will be more fully understood from the following detailed description take n in conjunction with the accompanying drawings, in which.

DETAILED DESCRIPTION OF THE INVENTION

Figure 1:
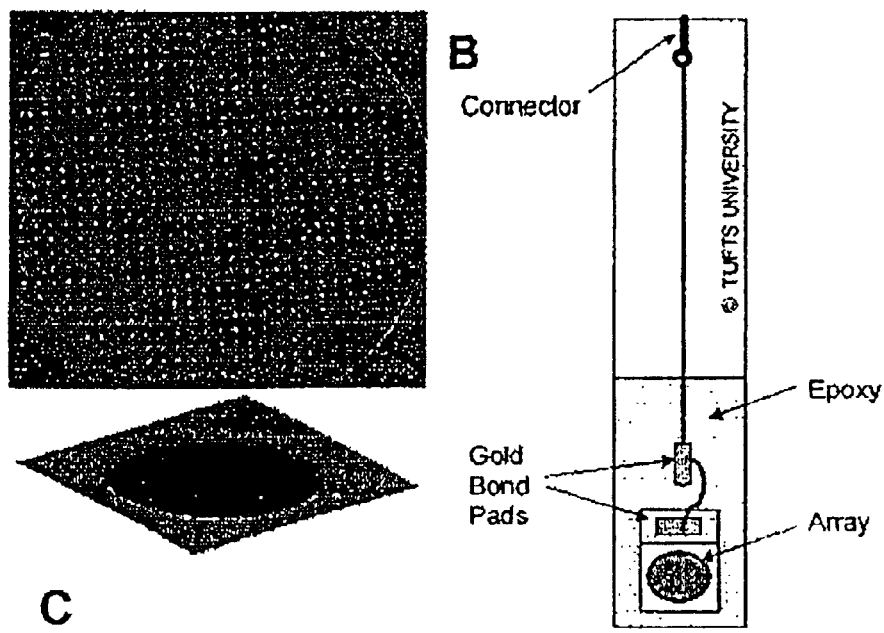
FIG 1. depicts: (A) an SEM image of an UMEA; (B) a schematic of a representative Ir-UMEA/PC-Board/Epoxy sensor; and (C) a n AFM image of an individual UME.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

This invention pertains to the discovery, characterization and use of an Ir-UME for the square wave anodic stripping voltammetry (SWASV) of $Cu^{2+}$ and $Hg^{2+}$ directly on iridium, in the form of a microfabricated array of UMEs, without the use of mercury. The use of iridium directly as an electrode substrate for the determination of copper (II) provides for the first time an acceptable electrode surface and eliminates the use of mercury. The direct use of iridium as an electrode for this purpose was unknown until the discovery of this invention. Experimental parameters such as supporting electrolyte, SW frequency, and deposition time, and deposition potential were optimized, and the response of the sensor to $Cu^{2+}$ in real samples are shown in the following sections and figures which follow.

In one aspect of the invention, an ultramicroelectrode includes: a) a metallic substrate; b) a first metallic oxide insulating layer; c) a first metallic adhesion layer; d) an iridium layer; e) a metallic bond pad layer; f) a second metallic adhesion layer; and g) a second metallic oxide insulating layer. The metallic substrate can be carbon, silicon, aluminum, phosphorous, gallium, indium, tin, antimony, selenium or germanium based., preferably silicon based. The first metallic oxide insulating layer can be a Group IV metallic oxide such as a Si, Ge, or Sn oxide, preferably a Si oxide. Typically the first metallic adhesion layer is a transition metal such as Ti, V, Cr, Sc, Nb, Mo, W, or, preferably Ti. The ultramicroelectrode also includes a metallic bond pad layer which can be Ni, Zn, Pd, Ag, Cd, Pt, Ga, In, or Au, preferably Au. The second metallic adhesion layer can be a transition metal such as Ti, V, Cr, Sc, Nb, Mo, W, or Ta, preferably Ti. The second metallic oxide insulating layer can be a Group IV metallic oxide such as Si, Ge, or Sn, preferably a silicone oxide. In preferred embodiment, the ultramicroelectrode of the invention does not include a mercury layer.

In certain aspects of the invention, one or more of the layers can be omitted from the ultramicroelectrode. The layers which can be eliminated can be determined by those skilled in the art and can include the omission of the first metallic oxide insulating layer and/or a second metallic adhesion layer and/or a second metallic oxide insulating layer; a first metallic adhesion layer and/or a second metallic adhesion layer and/or a second metallic oxide insulating layer; and a second metallic adhesion layer and/or a second metallic oxide insulating layer.

In a preferred embodiment, the ultramicroelectrode of the invention includes a) a silicon substrate; b) a silicon oxide insulating layer; c) a titanium adhesion layer; d) an iridium layer; e) a gold bond pad layer; f) a titanium adhesion layer; and g) a silicon dioxide insulating layer. In a preferred embodiment, the f) and g) layers have been partially or totally removed.

In still another embodiment, the present invention includes methods for producing an ultramicroelectrode by thermally growing a first metallic oxide insulating layer onto a metallic substrate followed by evaporating a first metallic adhesion layer onto the first metallic oxide layer. An iridium layer is the deposited onto the first metallic layer and a metallic bond pad layer is deposited onto the iridium layer. A second metallic adhesion layer is evaporated onto the metallic bond pad layer and a second metallic oxide insulating layer is then deposited onto the second metallic adhesion layer. Preferentially, a portion or all of the second metallic adhesion layer and second metallic oxide insulating layer is removed.

The term "ultramicroelectrode" is recognized by those skilled in the art and are generally those which has at least one dimension which is 20 $\mu$m or less. Thus, for example, an ultramicroelectrode can be a disk with a radius less than or equal to 20 $\mu$m, or a ring having its electrically conductive width less than or equal to this dimension. In contrast, a "microelectrode" is one that typically has dimensions on the order of one to several millimeters.

The ultramicroelectrodes of the invention can be used for electrochemical detection methods, including components of in vivo biosensors and in such processes as chromatography and capillary electrophoresis. The ultramicroelectrodes of the present invention can also be used in such applications such as in hospitals, where analysis can be performed without the need to continually drawn blood samples from an individual.

The term "metallic oxide" is recognized by those skilled in the art and is intended to include monooxides, dioxide, trioxides, etc. including those oxides which are not considered full integer values, that is the oxide has a value which falls between two integer values, e.g. 1.2, 1.25, 1.50, 1.79, 2,03, 2.64, etc.

The term "metallic bond pad layer" is recognized by those skilled in the art and includes those metals which are used for bonding with a substrate layer to permit bonding with wires with or without the use of conductive epoxies. Metallic bond pad layers are described in U.S. Pat. Nos. 5,174,883, 5,431,800 and 5,378,343, the contents of which are hereby expressly incorporated by reference.

EXPERIMENTAL SECTION

Apparatus

Square wave anodic stripping voltammetry (SWASV) was performed with an EG&G PAR Model 273 potentiostat/galvanostat (EG&G PAR, Princeton, N.J.) interfaced to a DEC p420-SX microcomputer using M270 software (EG&G PAR). All voltammetric experiments were performed in a three electrode cell consisting of an iridium ultramicroelectrode array (Ir-UMEA), a Ag/AgCl (3 M NaCl) reference electrode (Bioanalytical Systems, Inc., RE-5B or RE-6) and a Pt wire counter electrode. All potentials are reported relative to the Ag/AgCl (3 M NaCl) reference electrode. Surface topographies were obtained with a Nanoscope E atomic force microscope (Digital Instruments, Santa Barbara, Calif.).

Reagents

All solutions were prepared with 18 MW·cm deionized water from a Barnstead Nanopure system (Barnstead Co., Dubuque, Iowa). Metal solutions were prepared with 99.999+% Cu(NO3)2 and Hg(NO3)2 (Johnson Matthey). Electrolyte solutions were prepared with trace metal grade sulfuric acid, perchloric acid, nitric acid, and hydrochloric acid (Fisher). Potassium nitrate solutions were prepared with 99.999+% KNO3 (Johnson Matthey). All other solutions were prepared with ACS grade reagents. Glassware was stored in 8 M HNO3 for one week and rinsed thoroughly with deionized water. Unless otherwise stated, all runs were performed in triplicate and the numbers reported are the average of those runs.

Fabrication of the Ir-UME Arrays

Fabrication was performed at the IBM, T. J. Watson Research Center (Yorktown Heights, N.Y.) and involved the following process steps. A 5000 Å oxide layer was thermally grown on a standard five-inch silicon wafer. After patterning, sequential electron beam evaporation steps were used to deposit an adhesion layer of Ti (100 Å) followed by an Ir layer (2000 Å). This was followed by a Au layer (5000 Å) used for the bonding pads. The Ir deposition step was performed at an elevated temperature in order to reduce the tensile stress in the film. This step is very crucial since improper deposition promotes cracking and flaking of the Ir surface. A second layer of Ti was deposited on top of the metal to insure adhesion to the insulating layer.

Photolithographic stenciling was used to outline the ultramicroelectrode pattern and an Ar+ ion beam etch was used to transfer the stencil. Reactive RF-diode sputter deposition was used to deposit a 5000 Å SiO2 insulating layer. Reactive ion etching was used to remove the SiO2 in the desired pattern for the UME array and the bond pad. Additionally, an Ar+ ion beam was used to remove the top titanium layer on the top surface to expose the disks and the bond pad. FIG. 1A shows an SEM image of an UME array. There are 564 individual UMEs per array separated by 68 m (center-to-center) and one array per chip, giving a total electroactive surface area of 6.3710-4 cm2. An AFM image of a single 12 m diameter UME is shown in FIG. 1C. The wafer was cleaned and diced into 3.4 3.1 mm chips that were then glued onto a custom designed printed circuit board (CFC, Waltham, Mass.) with an epoxy (EpoTek 905, Epoxy Technology, Billerica, Mass.). Electrical connection between the chip and the circuit board was made by a 1.25 m Au wire (99.99% Williams Advanced Materials, Buffalo, N.Y.). The epoxy (Orion Research, Inc. Beverly, Mass.) was applied around the chip to insulate and protect the Au wire and the PC board from the solution (FIG. 1B). After application, the epoxy was cured for 2 hours at 50C.

Optimization of Parameters for Cu2+ Determination

Eight different electrolytes were investigated to establish a suitable media for determination of Cu2+ directly on the Ir substrate using SWASV. These included 0.1 M solutions of HNO3, KNO3, HClO4, HCl, H2SO4, 0.5 M NaCl, and a pH 4.8 Acetate Buffer, all containing 50 ppb of Cu2+. The parameters used for SWASV were: initial potential (Ei)

−0.3V, final potential (Ef) 0.45 V, deposition time (td) 180 s (stirred), equilibration time (teq) 15 s, frequency (f) 180 Hz, pulse amplitude (Esw) 25 mV, and step height (DEs) 2 mV. The lowest SWASV peak stripping responses (760-600 nA) were obtained in the chloride media, most likely due to the increase in the stability of Cu+ complexes. When the 0.5 M NaCl electrolyte was acidified (pH 2) the peak response decreased even further (379 nA). A lower response was also observed with 0.1 M HNO3 compared to 0.1 M KNO3 (1060 vs. 1660 nA). This was most likely due to hydrogen evolution interfering with the deposition of copper on the iridium surface. No stripping peak for copper was obtained in the acetate buffer even after increasing the deposition time to 300 s and the concentration to 150 ppb. From the results of these experiments, three electrolytes were chosen to further evaluate copper determination: 0.1 M HClO4, 0.1 M KNO3, and 0.1 M H2SO4, all containing 50 ppb of Cu2+.

The deposition potential was optimized for each electrolyte in order to eliminate any interference from hydrogen evolution. For the more acidic electrolytes, 0.1 M HClO4 and H2SO4, the optimum deposition potential was −0.35 V and −0.3 V, respectively. For the 0.1 M KNO3 electrolyte, the optimum deposition occurred more cathodic at −0.4 V.

Figure 2:
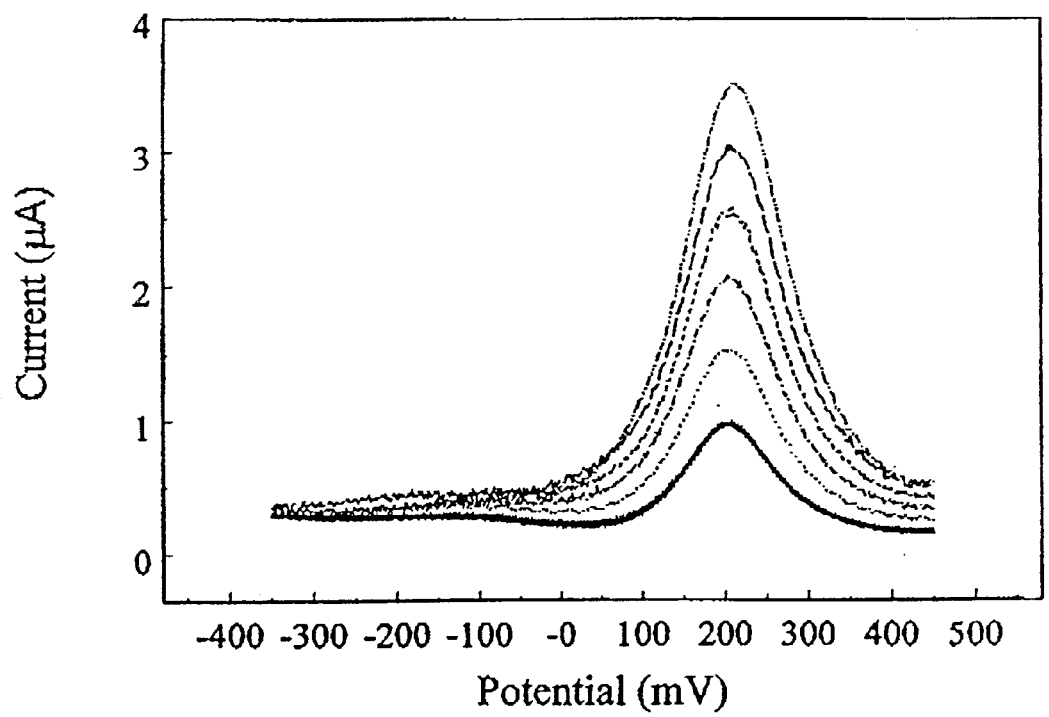
FIG. 2. shows a current response of the Ir-UMEA when varying the SW frequency from 120 to 420 Hz for a solution containing 50 ppb $Cu^{2+}$ and 0.1 M $HClO_4$. SWASV parameters: $Ei=-0.35$ V, $Ef=0.45$ V, $td=180$ s, $teq=15$ s, $Esw=25$ mV, and $DEs=2$ mV. $f=120$ Hz (—), 180 Hz ( . . . . . . . . ) 240 Hz (-. -. -), 300 Hz (- - -), 360 Hz (— —), and 420 Hz (- . . . - . . . -).

In SWASV several parameters effect the peak stripping current, these include frequency (f), pulse amplitude (Esw) and step height (DEs). The frequency was varied from 120 to 420 Hz in a solution consisting of 50 ppb Cu2+ and 0.1 M HClO4. The stripping peak current response when varying the frequency is shown in FIG. 2. Excellent linearity was observed, over the entire 300 Hz range, between f and the average stripping peak current (R2=1.000). A frequency of 300 Hz was used for all subsequent experiments.

The deposition time (td) was varied from 60 to 360 s in the three different electrolytes that contained 50 ppb Cu2+. Good linearity was obtained in all electrolytes with the lowest regression coefficient (R2=0.989) for the data taken using the 0.1 M KNO3 electrolyte. In this electrolyte, at higher deposition times, there was a slight distortion and shift of the copper stripping peak, and could account for the lower regression coefficient. In the 0.1 M H2SO4 a secondary peak was observed at −0.1 V. This peak decreased with increasing td and can be attributed to the under potential deposition peak for hydrogen on the iridium surface. However, this peak did not interfere with copper determination since excellent linearity (R2=1.000) was obtained in this electrolyte. Good linearity (R2=0.997) was also obtained in the 0.1 HClO4 electrolyte when varying the deposition time.

Reproducibility for Cu2+

Figure 3A:
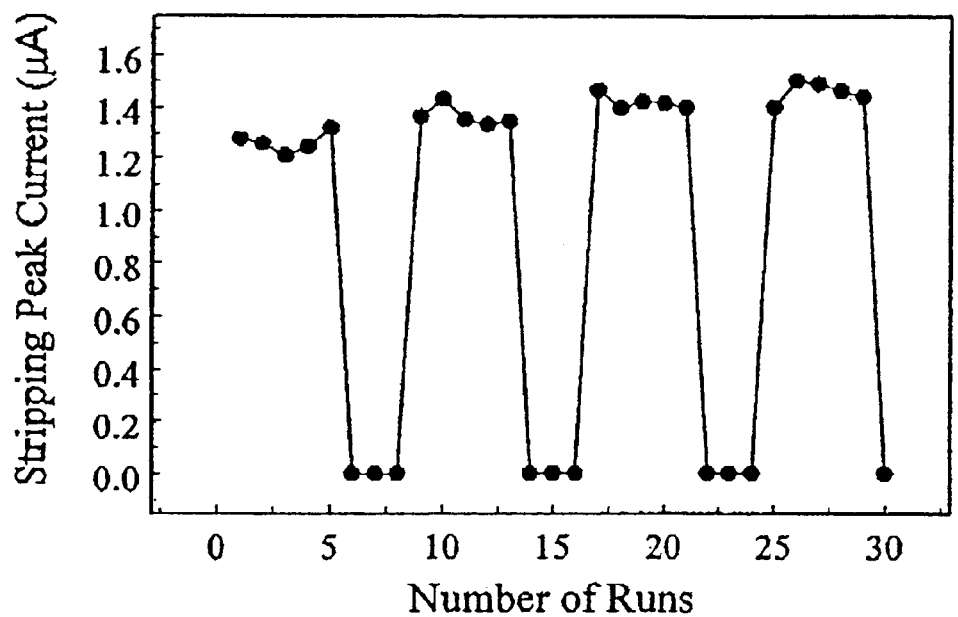
FIG. 3. is a reproducibility study when varying the following parameters: (A) Deposition time td (0 and 180 s) in a solution of 50 ppb $Cu^{2+}$ and 0.1 M $KNO_3$, with $Ei=-0.4$ V, $Ef=0.45$ V, $teq=15$ s, $f=300$ Hz, $Esw=25$ mV, and $DEs=2$ mV; and (B) $Cu^{2+}$ concentration (20 ppb and 50 ppb) in 0.1 M $HClO_4$, with $Ei=-0.35$ V, $Ef=0.45$ V, $td=120$ s, $teq=15$ s, $f=300$ Hz, $Esw=25$ mV, and $DEs=2$ mV.

When using a solid electrode substrate, which cannot be physically polished, two concerns arise; the reproducibility and the renewability of the electrode surface. Both td and the concentration of Cu2+ were varied to confirm that the iridium surface was not exhibiting any "memory effects" due to the deposition and stripping of copper. In a solution consisting of 50 ppb Cu2+ and 0.1 M KNO3, td was varied between 180 and 0 s (FIG. 3A). Five runs were performed for td=180 s and then three runs were performed with td=0 s. This was repeated four times to ensure that the copper response was reproducible and stable. When td=0 s, no copper stripping peak was observed, verifying that all the deposited copper was removed from the iridium surface by the anodic scan. When td=180 s the average peak height was 1.38 mA and over for those twenty runs the relative standard deviation was 1.3%. This demonstrated that the copper stripping peak was reproducible with little variation and that the copper was adequately removed from the iridium surface during the anodic scan.

Figure 3B:
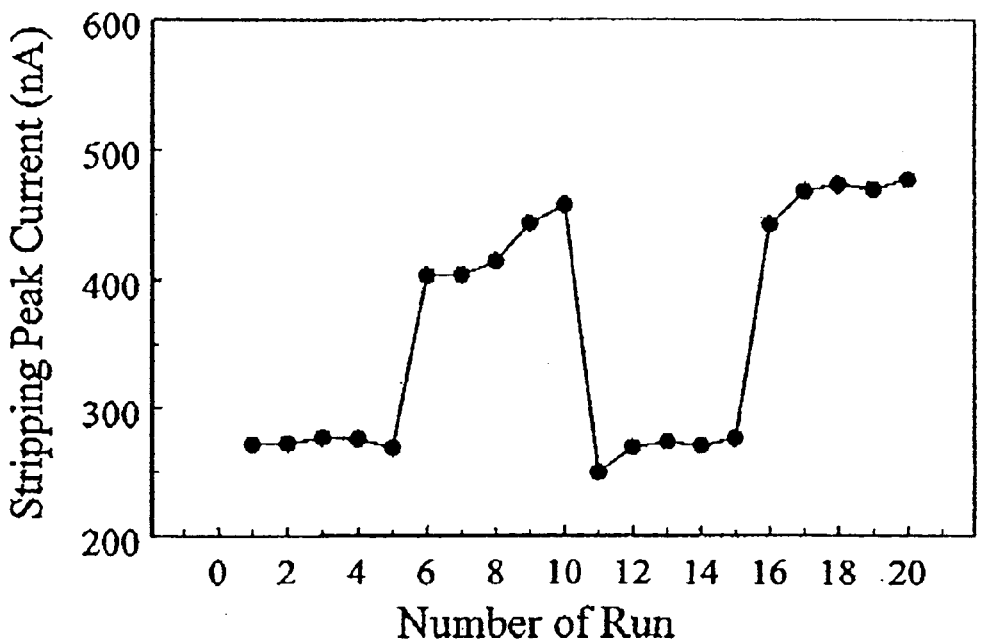

The reproducibility of the copper signal was also examined by varying the copper concentration (20 ppb and 50 ppb) in 0.1 M HClO4, and keeping all other parameters consistent. Five runs were performed in the 20 ppb solution and then the electrode was transferred to the 50 ppb solution and five runs were performed in this solution (FIG. 3B). This was performed twice. When transferring the array it was thoroughly rinsed with deionized water to limit cross contamination. There was some variation in first five runs in the 50 ppb solution but it was found to stabilize in a second set of runs. The average stripping peak currents for the ten runs of each concentration were 270.4 and 445.3 nA for the 20 and 50 ppb Cu2+ solutions, respectively. The relative standard deviations were 0.9% for the 20 ppb and 2.0% for the 50 ppb Cu2+ solution. Overall, the stripping peaks were stable and reproducible when varying the copper concentration. The peak height varied with the copper concentration in the solution and the array demonstrated a reliable and reproducible signal.

Calibration Curves for Cu2+

Calibration curves in the range of 20 to 100 ppb Cu2+ were generated with td=120 s for the 0.1 M H2SO4 electrolyte and td=180 s for the 0.1 M HClO4 and KNO3 electrolytes. Excellent linearity was obtained for all three electrolytes. Some peak distortion was observed with the KNO3 electrolyte, but did not appear to effect the copper response. The secondary peak at −0.1 V was still observed in the H2SO4 electrolyte but again did not influence the copper response and decreased with increasing copper concentration. Overall, the best results were obtained in the sulfuric acid (slope=1.45e−2 mA/ppb, y-intercept=−2.34e−2 mA and R2=0.999) and perchloric acid (slope=3.09e−2 mA/ppb, y-intercept=−0.369 mA and R2=0.999). The lowest regression coefficient (slope=3.93e−2 mA/ppb, y-intercept=−0.502 mA and R2=0.997) was obtained with the potassium nitrate electrolyte but it was still acceptable.

The detection limit was calculated for the three electrolytes from the calibration curve data. The calculated detection limit (S/N=3) was 1 ppb for 0.1 M KNO3 and 0.1M HClO4 and 5 ppb for 0.1 M H2SO4. The detection limit greatly depends on other parameters such as the deposition time (180 s for 0.1 M HClO4 and 0.1 M KNO3 and 12 s for 0.1 M H2SO4) and the frequency (300 Hz). Increasing the deposition time or the frequency can easily lower the detection limit of the Ir-UMEA.

Interference Studies for Cu2+

The interference of Zn, Cd, Pb, Ag and Hg on the copper stripping peak was investigated because these are all known to form intermetallic complexes with copper. These metals can be categorized in two different groups: (I) those that have a redox potential more anodic than copper (Ag and Hg) and (II) those that have a redox potential more cathodic than copper (Zn, Cd, and Pb). The interference study was performed in a solution containing 50 ppb Cu2+ and 0.1 M HClO4. The addition of 50, 100 and 500 ppb of the interfering metal was made to the copper solution and the normalized peak stripping current was calculated to determine the influence of the interfering metal. The first group of interfering metals (Ag and Hg) drastically influenced the copper signal even at 50 ppb. With the addition of silver the copper peak was distorted and a reproducible signal could not be obtained. When mercury ions were introduced into the solution, the copper signal kept increasing and did not level off even after ten runs. The second group of interfering metals (Zn, Cd, and Pb) had a smaller affect on the copper stripping peak. A small decrease (14%) was observed when 500 ppb Pb or Cd were in the copper solution and a small increase (8%) was observed when 500 ppb Zn was added to the copper solution. The addition of the metals did not influence the overall shape of the copper peak, except for the addition of 500 ppb Pb, where a small shoulder was observed on the copper signal.

Application to Real Samples for Cu2+

Tap water and bottled drinking water samples were analyzed for copper using an Ir-UMEA and the results compared to a Hg-plated glassy carbon electrode (Hg-GCE). The tap water sample was taken directly from a faucet in the laboratory and acidified to pH 1 with perchloric acid. A sample of Poland Spring drinking water was also acidified in the same manner. The standard addition method was used to determine the concentration Cu2+ in the sample.

Figure 4:
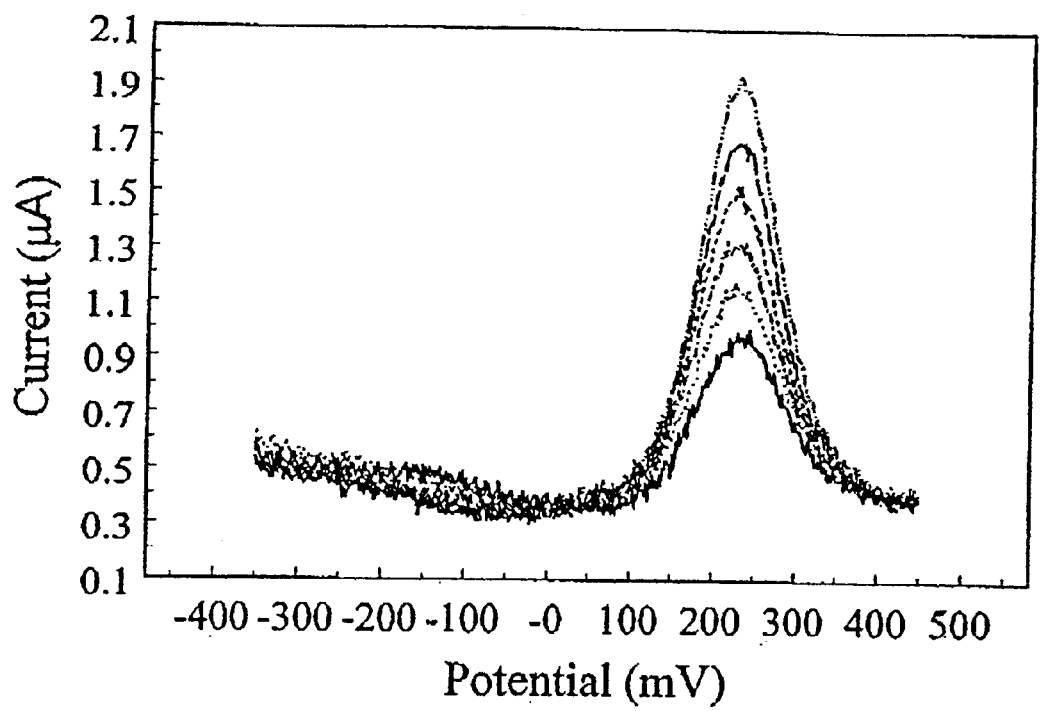
FIG. 4 shows current responses for five standard addition of 100 ppb $Cu^{2+}$ to an acidified tap water sample with the Ir-UMEA. SWASV parameters: $Ei=-0.35$V, $Ef=0.45$V, $td=30$ s (unstirred), $f=300$ Hz, $Esw=25$ mV, and $DEs=2$ mV. Sample (—), 100 ppb added ( . . . . . ), 200 ppb added (-.-.-), 300 ppb added (- - -), 400 ppb added (— —), and 500 ppb added (- . . . - . . . -)

The tap water was analyzed directly on an Ir-UMEA by SWASV using the following parameters: $E_i=-0.35$ V, $E_f=0.45$ V, $t_d=3$ s (unstirred), $f=300$ Hz, $E_{sw}=25$ mV, and $DE_s=2$ mV. The sample was spiked five times with 100 ppb Cu2+. The voltammograms of the standard additions are shown in FIG. 4. The plot of the average peak stripping current (mA) versus the concentration of Cu2+ added (ppb) gave a regression coefficient of 0.999, and a slope and y-intercept of 1.90110-3 and 0.6159, respectively. The concentration of Cu2+ in the tap water was calculated to be 324 ppb. The concentration, determined using a Hg-GCE, was found to be 354 ppb. The difference between the two methods is within experimental error.

Figure 5:
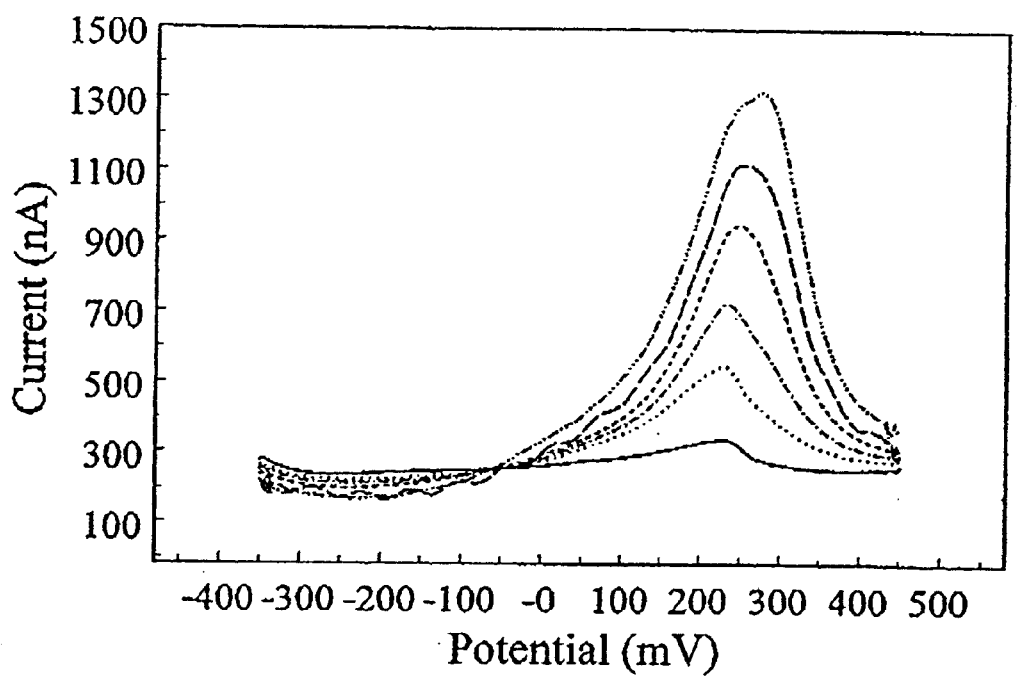
FIG. 5 depicts representative current responses for five standard addition of 10 ppb $Cu^{2+}$ to an acidified Poland Springs drinking water sample with the Ir-UMEA. SWASV parameters: $Ei=-0.35$V, $Ef=0.45$ V, $td=180$ s (stirred), $teq=15$s, $f=300$ Hz, $Esw=25$ mV, and $DEs=2$ mV. Sample (—), 10 ppb added ( . . . . . ), 20 ppb added (-.-.-), 30 ppb added (- - -), 40 ppb added (— —), and 50 ppb added (- . . . - . . . -)

The Poland Spring bottled drinking water was analyzed using the same parameters as above except that the deposition time was increased to 18 s (stirred). The sample was spiked five times with 10 ppb Cu2+. The voltammograms of the standard additions are shown in FIG. 5. The plot of the average peak stripping current (nA) versus the concentration of Cu2+ added (ppb) gave a regression coefficient of 0.999, and a slope and y-intercept of 19.46 and 98.89, respectively. The calculated concentration of Cu2+ in the Poland Spring drinking water was 5.1 ppb. Using the Hg-coated GCE, the copper concentration was determined to be 5.9 ppb. The difference of 0.8 ppb demonstrates excellent reliability of the bare Ir-UMEA for determining Cu2+ in water. The concentration of copper in the Poland Spring water sample was near the calculated detection limit for the Ir-UMEA. The average peak stripping current for the sample was 94.9 nA, which can be increased by increasing the deposition time, however, since a good peak response was obtained, it was not further increased.

Optimization of parameters for Hg2+ determination

A solution containing 0.1M KSCN was chosen as the electrolyte to insure that the redox potential of Hg2+ would fall within the potential window of iridium. This electrolyte complexes the mercury ions in solution and is often used as a stripping medium for mercury film electrodes3, 4 and give a stripping peak for mercury at about 0 mV, well within the potential window of iridium.

The deposition potential ($E_d$) was optimized in a solution containing 50 ppb Hg2+ and 0.1 M KSCN, $E_d=0.5$ V and for <10 ppb Hg2+, $E_d=-0.6$ V. Even though hydrogen evolution was not observed at either of these potentials, the background current increased at the more negative potential.

Figure 6:
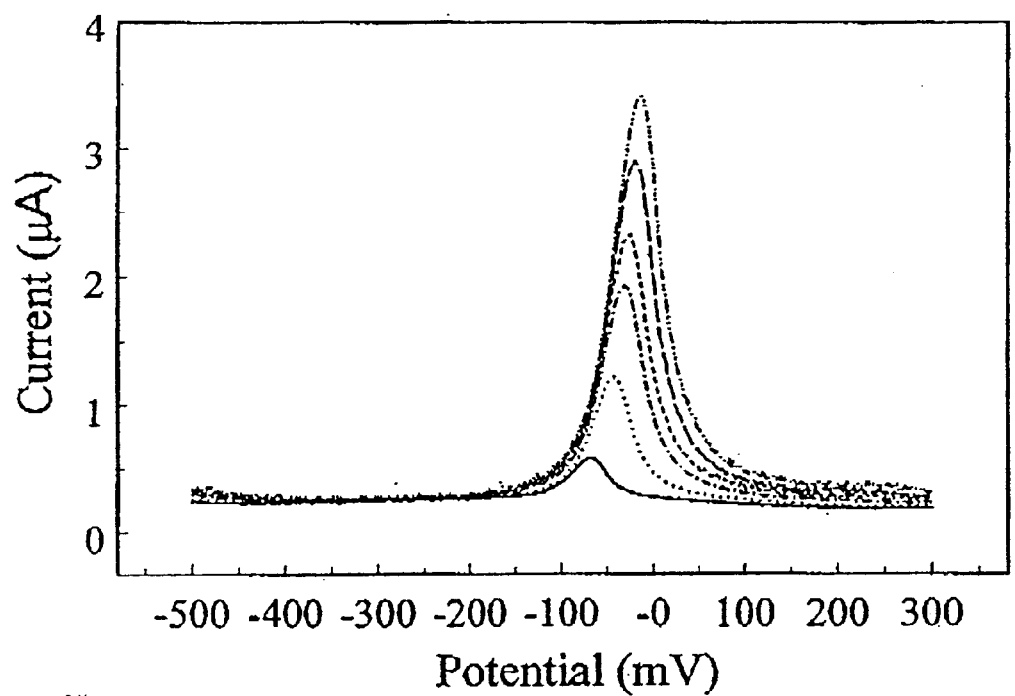
FIG. 6. depicts representative current responses of the Ir-UMEA for varying the td from 60 s to 360 s in a solution containing 50 ppb $Hg^{2+}$ and 0.1 M KSCN. SWASV parameters: $Ei=-0.5$V, $Ef=0.3$ V, $teq=15$ s, $f=360$ Hz, $Esw=50$ mV, and $DEs=2$ mV, $td=60$ s (—), 120 s ( . . . . . . ), 180 s (-.-.-), 240 s (- - -), 300 s (— —), and 360 s (- . . . - . . . -)

The deposition time was varied from 60 to 360 s for the 50 ppb Hg2+ solution and from 360 to 720 s for the 1 ppb Hg2+ solution. In both cases, the peak stripping current increased with the deposition time. FIG. 6 shows the typical shape of the voltammograms obtained with the 50 ppb Hg2+ solution for $60<t_d<360$ s. The SWASV parameters used were $E_i=-0.5$ V, $E_f=0.3$ V, $t_{eq}=15$ s, $f=360$ Hz, $E_{sw}=50$ mV, and $DE_s=2$ mV. Plotting the average peak stripping current (mA) versus the deposition time (s) gave a regression coefficient of 0.997 and a slope and y-intercept of 8.90410-3 and 4.59310-2, respectively. For the 1 ppb Hg2+ solution, the initial potential was changed to -0.6 V and all the other parameters were same as for the 50 ppb solution. The deposition time was varied from 360 to 720 s. The y-intercept, slope and regression coefficient were -0.7278, 2.56510-3 and 0.998, respectively, for a plot of the average peak stripping current versus td. Thus, for both concentrations of mercury, the signal varied linearly with the deposition time in the range that was examined.

Reproducibility Study for Hg2+

As with the determination of copper, it is very important to determine if the deposition and stripping of mercury has any "memory effects" on the iridium surface. Using a solution of 50 ppb Hg2+ and 0.1 M KSCN, five runs were made with $t_d=120$ s and then three runs with $t_d=0$ s. This was repeated twice to guarantee that the mercury response was reproducible and stable. No indications of any mercury were seen for $t_d=0$ s, confirming that the mercury was completely removed from the iridium surface by the anodic scan. For $t_d=120$ s, the average peak stripping current was 2.02 mA with a relative standard deviation of 3.4% for ten repetitions. Thus, the mercury stripping peak is reproducible and the anodic scan adequately removes the mercury from the iridium surface.

Calibration Curves for Hg2+

Figure 7:
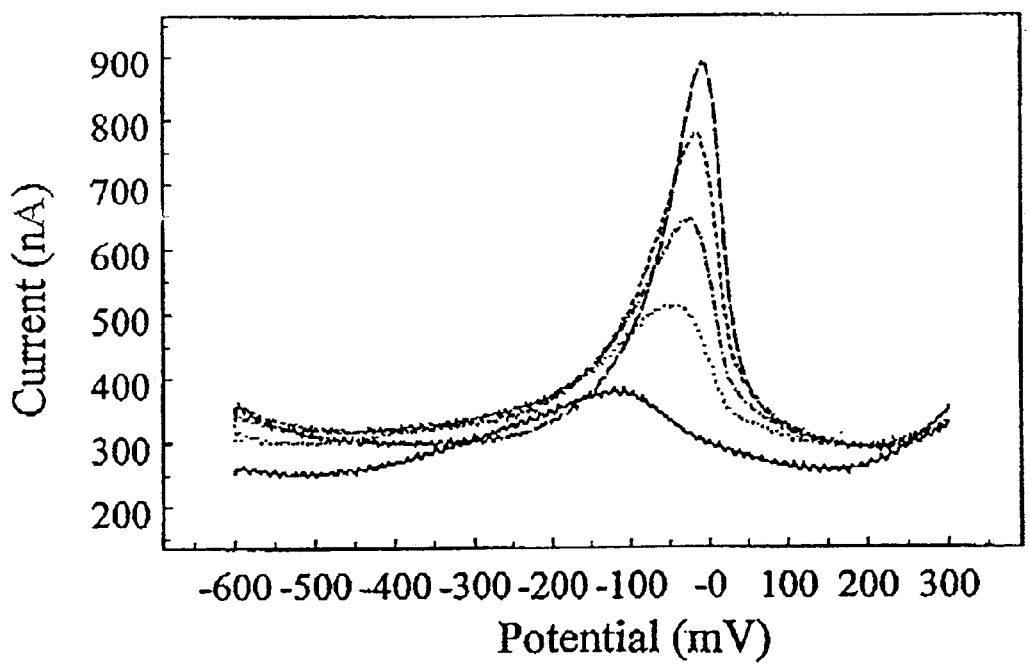
FIG. 7. depicts representative current responses of the Ir-UMEA for concentrations of $Hg^{2+}$ from 1 ppb to 9 ppb in 0.1 M KSCN. SWASV parameters: $Ei=-0.6$ V, $Ef=0.3$ V, $td=360$ s (stirred), $teq=15$ s, $f=360$ Hz, $Esw=50$ mV, and $DEs=2$ mV. 1 ppb (—), 3 ppb ( . . . . . . ), 5 ppb (-.-.-), 7 ppb (- - -), and 9 ppb (— —)

Unlike the copper, it is very important to be able to determine mercury at concentrations of <10 ppb. Therefore, a calibration curve from 1 to 9 ppb Hg2+ was generated. The SWASV parameters used were $E_i=-0.6$ V, $E_f=0.3$ V, $t_d=360$ s (stirred), $t_{eq}=15$ s, $f=360$ Hz, $E_{sw}=50$ mV, and $DE_s=2$ mV. FIG. 7 shows voltammograms for 1, 3, 5, 7, and 9 ppb Hg2+ in 0.1 M KSCN. The plot of the average peak stripping current versus the mercury concentration resulted in a regression coefficient of 0.997. The slope and y-intercept were 58.902 and 58.585, respectively. The signal for 1 ppb Hg2+ was 131 nA, indicating that it was near the detection limit for this 360 s deposition time. The calculated detection limit (S/N=3 and $t_d=36$ s) was 0.6 ppb.

Figure 8:
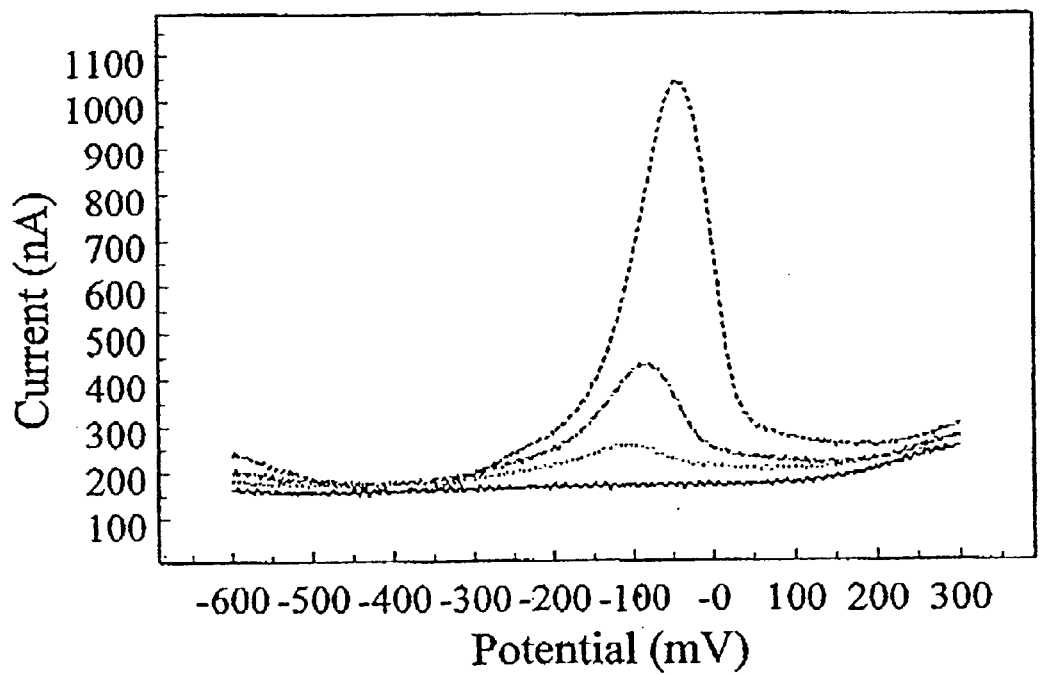
FIG. 8. depicts representative current responses of the Ir-UMEA for a blank, 100 ppt, 500 ppt and 1000 ppt $Hg^{2+}$ in 0.1 M KSCN. SWASV parameters: $Ei=-0.6$ V, $Ef=0.3$ V, $td=600$ s (stirred), $teq=15$ s, $f=360$ Hz, $Esw=50$ mV, and $DEs=2$ mV. Blank (—), 100 ppt ( . . . . . . ), 500 ppt (-.-.-), and 1000 ppt (- - -)

To achieve determination of mercury with the Ir-UMEA in the parts-per-trillion (ppt) range, the deposition time must be increased. This was demonstrated by setting $t_d=600$ s and using solutions containing 0, 100, 500, and 1000 ppt Hg2+ (FIG. 8). The calculated detection limit with a deposition time 600 s (S/N=3) was 85 ppt Hg2+. The stripping peak current observed for the 100 ppt Hg2+ was 66 nA, which was close to the calculated detection limit.

Interference Studies for Hg2+

The interference of Zn, Cd, Pb, and Cu on the mercury stripping peak was investigated. The interference studies were performed in a solution containing 50 ppb Hg2+ and 0.1 M KSCN. The interfering metal (50, 100 and 500 ppb) was added to the mercury solution. To determine the influence of the interfering metal, the normalized stripping peak current was calculated. Zn, Cd, Pb and Cu had small effects on the mercury peak at 50 and 100 ppb. At 500 ppb a decrease in the mercury stripping peak was observed, the normalized stripping peak current was 73%, 75% and 67% for Zn, Cd, and Pb, respectively. Copper, at 500 ppb, obscured the mercury stripping peak, therefore, the peak could not be observed.

Application to Real Samples for Hg2+

Drinking water was analyzed directly on an Ir-UMEA by SWASV using the following parameters: Ei=−0.5 V, Ef=0.3 V, td=24 s (stirred), f=360 Hz, Esw=50 mV, and DEs=2 mV. The sample was prepared in 0.1 M KSCN. No mercury was found in the drinking water. To demonstrate that mercury could be determined in the real sample five spikes of 10 ppb Hg2+ were performed. The plot of the average peak stripping current (nA) versus the concentration of Hg2+ added (ppb) gave a regression coefficient of 0.999, and a slope and y-intercept of 11.275 and −6.3785, respectively. A sample of tap water was also spiked with mercury but a calibration curve could not be obtained because of the large amount of copper present in the sample.

Changes in the Iridium Surface

During the initial experiments, after approximately 70 runs the Ir-UMEA could no longer be used to detect Cu2+ or Hg2+. Since no visible changes could be seen on the surface of the iridium microelectrodes, atomic force microscopy (AFM) was used to further characterize their topography. The surfaces of the microdisks were imaged before and after the array failed to respond. The AFM images showed a definite change in the overall topography, with the roughness of the iridium surfaces increasing by a factor of 3.

Figure 9:
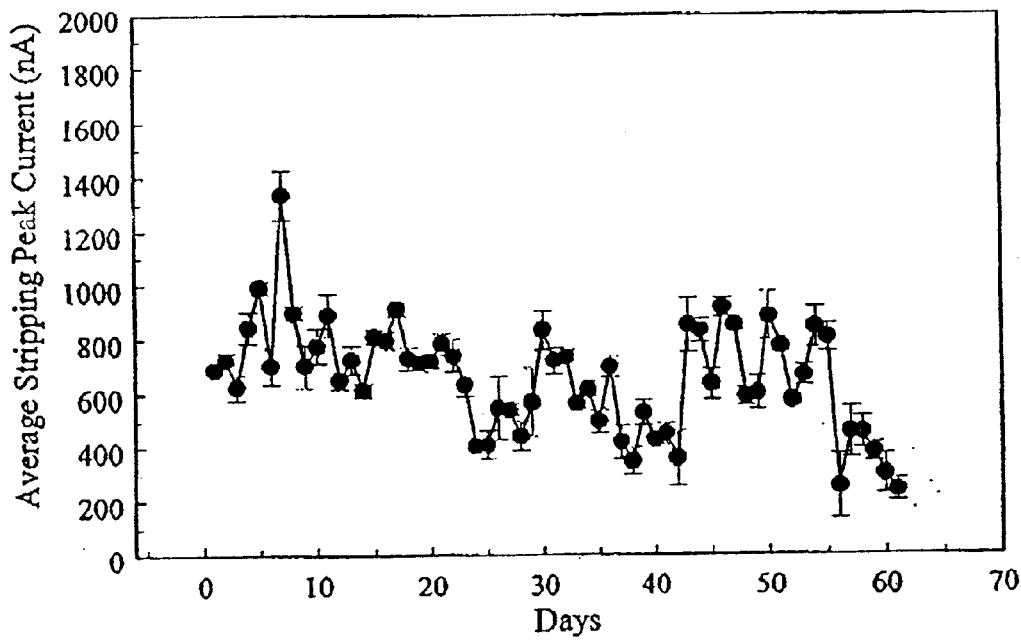
FIG. 9. is a diagram representative of the peak stripping current response of an Ir-UMEA for 250 ASV runs over 60 days using a solution of 50 ppb $Cu^{2+}$ in 0.1 M $H_2SO_4$.

Preliminary investigation indicated that failure of the array was the result of chloride leakage from the reference electrode. When using a macro-reference electrode with a porous vycor junction (RE-5B), a sharp secondary peak occurred on the copper signal after approximately 30 runs. This secondary peak was also observed when using a gold electrode and was therefore not an attribute of the iridium substrate. A smaller reference electrode (RE-6) was used which decreased the chloride leakage to the sample solution. The response of the Ir-UMEA was dramatically influenced because the array functioned for over 200 runs with little degradation of the copper peak (average 1040 nA with a relative standard deviation of 1.2%). After approximately 250 runs some degradation of the peak was observed but the array was still able to detect copper. Considering that the iridium surface cannot be polished or regenerated, 250 runs are acceptable for usage of the Ir-UMEA as a disposable sensor. The copper peak stripping current was also monitored for over sixty days of continual use (FIG. 9). Each day ten runs of a solution containing 50 ppb Cu2+ and 0.1 M H2SO4 were performed. A relatively stable and reproducible signal was obtained for the first 25 days. Thereafter the response began to vary more significantly from day to day. After 50 days of use the signal degraded about four times its original value. These results demonstrate that the Ir-UMEA can be used to monitor copper continuously for a reasonable period of time.

The invention demonstrates that microfabricated Ir-UMEAs are suitable and reliable substrates for the SWASV of copper and mercury ions. For determination of copper, excellent linearity of the peak stripping current was obtained when varying the frequency, deposition time, and copper concentration, from 20 to 100 ppb. The single copper stripping peak demonstrated good reliability, reproducibility and stability. Real samples of low (5 ppb) and high (324 ppb) concentrations of copper were easily determined by altering the deposition time. Good agreement between the Ir-UMEA and Hg-GCE was also obtained for real samples of tap water and drinking water. For determination of mercury excellent linearity was obtained when varying the deposition time in a 50 ppb Hg2+ and 1 ppb Hg2+ sample. Good linearity was also obtained when varying the mercury concentration from 1 ppb to 9 ppb. Some deformations in the copper signal were observed but only in the KNO3 electrolyte. However, multiple stripping peaks were not observed for either copper or mercury. The observed detection limits, 5 ppb Cu2+ (td=180 s) and 100 ppt for Hg2+ (td=600 s), were in excellent agreement with the calculated detection limits, 1 ppb and 100 ppt respectively. Increasing the deposition time or SWV parameters such as frequency or pulse amplitude would produce even lower detection limits. An unexplained effect of chloride ions on the iridium surface was observed, but it was found to be insignificant when chloride leakage from the reference electrode was minimized.

References (1) Herdan, J.; Feeney, R.; Kounaves, S. P.; Flannery, A. F.; Storment, C. W.; Kovacs, G. T. A.; Darling, R. B. Environ. Sci. Technol. 1998, 32, 131–136.

(2) Feeney, R.; Herdan, J.; Nolan, M.; Tan, S.; Tarasov, V.; Kounaves, S. P. Electroanalysis, 1998, 10, 89–93.

(3) Belmont, C.; Tercier, M.-L.; Buffle, J.; Fiaccabrino, G. C.; Koudelka-Hep, M. Anal. Chim. Acta. 1996, 329, 203–214.

(4) Kounaves, S. P.; Deng, W.; Hallock, P. R.; Kovacs, G. T.; Storment, C.; Anal.Chem., 1994, 66, 418–423

(5) Wang, E.; Sun, W.; Yang, Y. Anal. Chem. 1984, 56, 1903–1906.

(6) Baldo, M. A.; Bragato, C.; Mazzocchin, G. A.; Daniele, S. Electrochim. Acta 1998, 43, 3413–3422.

(7) Wang, F.; Li, S.; Liu, S.; Zhang, Y.; Liu, Z. Anal. Lett. 1994, 27, 1779–1787.

(8) Beltowska-Brzezinska, M.; Lulek, J.; Klonowska, D.; Grochmalicka-Makolajczyk, J. Chem. Anal. (Warsaw) 1993, 38, 527–534.

(9) Uhlig, A.; Schnkenberg, U.; Hintsche, R. Electroanalysis 1997, 9, 125–129.

(10) Williams, G.; D'Silva, C. Analyst 1994, 119, 2337–2341.

(11) Tercier, M.-L.; Buffle, J.; Zirino, A.; De Vitre, R. R. Anal. Chim. Acta 1990, 237, 429–437.

(12) Fakhari, A. R.; Ganjali, M. R.; Shamsipur, M. Anal. Chem. 1997,69, 3693–3696.

(13) Cai, X.; Kalcher, K.; Diewald, W.; Neuhold, C.; Magee, R. J. Fresenius J. Anal. Chem. 1993, 345, 25–31.

(14) Sousa, M.; Bertazzoli, R. Anal. Chem. 1996, 68, 1258–1261.

(15) Kim, H.-J.; Park, D.-S.; Hyun, M.-H.; Shim, Y.-B. Electroanalysis 1998, 10, 303–306.

(16) Zen, J.-M.; Chung, M.-J. Anal. Chem. 1995, 67, 3571–3577.

(17) Ugo, P.; Moretto, L. M.; Mazzocchin, G. A. Anal. Chim. Acta 1995, 305, 74–82.

(18) Ugo, P.; Sperni, L.; Moretto, L. M. Electroanalysis 1997, 9, 1153–1158.

(19) Hatle, M. Talanta 1987, 34, 1001–1007.

(20) Jaya, S.; Rao, T. P.; Roa, G. P. Analyst 1985, 110, 1361–1364.

(21) Wang, J.; Tian, B.; Lu, J.; Wang, J.; Luo, D.; MacDonald, D. Electroanalysis 1998, 10, 399–402.

(22) Gustavsson, I. J. Electroanal. Chem. 1986, 214, 31–36.
(23) Rievaj, M.; Mesaros, S.; Bustin, D. Anales de Quimica 1993, 347, 347–350.
(24) Viltchinskaia, E. A.; Zeigman, L. L.; Garcia, D. M.; Santos, P. F. Electroanalysis 1997, 9, 633–640.
(25) Jeong, E.; Won, M.; Shim, Y. Electroanalysis 1994, 6, 887–893.
(26) Agraz, R.; Sevilla, M. T.; Hernandez, L. Anal. Chim. Acta 1993, 273, 205–212.
(27) Rievaj, M.; Mesaros, S.; Bustin, D. Collect. Czech. Chem. Commun. 1993, 58, 2918–2923.
(28) Gil, E. P.; Ostapczuk, P. Anal. Chim. Acta 1994, 293, 55–65.
(29) Sipos, L.; Golimowski, J.; Valenta, P.; Numburg, H. W. Fresenius Z. Anal. Chem. 1979, 298, 1–8.

One skilled in the art will appreciate further features and advantages of the invention based on the above-described embodiments. Accordingly, the invention is not to be limited by what has been particularly shown and described, except as indicated by the appended claims. All publications and references cited herein, including those in the background section, are expressly incorporated herein by reference in their entirety.

What is claimed is:

1. An ultramicroelectrode array, the array comprising:
   a) a substrate;
   b) an iridium layer deposited over and insulated from the substrate, said iridium layer including an exposed portion comprising an exposed iridium ultramicroelectrode surface; and
   c) a metallic bond pad layer, the metallic bond pad layer including a pattern of at least one bond pad interconnected to the exposed iridium ultramicroelectrode surface via a conductive pathway,
      wherein the ultramicroelectrode array is configured such that, when used in association with a reference or counter electrode for detecting metal concentration in a fluid, dipping the array in fluid places said exposed iridium ultramicroelectrode surface directly in contact with the fluid whereby a potential applied to the bond pads deposits or strips metal present in the fluid to produce a signal indicative of metal concentration in the fluid.

2. The ultramicroelectrode array of claim 1, wherein said substrate includes a carbon, silicon, aluminum, phosphorous, gallium, indium, tin, antimony, selenium or germanium substrate.

3. The ultramicroelectrode array of claim 1, wherein said substrate is a silicon substrate.

4. The ultramicroelectrode array of claim 1, wherein said substrate is metallic and further comprising an insulating layer between the substrate and the iridium layer.

5. The ultramicroelectrode array of claim 4, wherein said insulating layer is a Group IV metallic oxide.

6. The ultramicroelectrode array of claim 5, wherein said Group IV metallic oxide is a Si oxide.

7. The ultramicroelectrode array of claim 4, further comprising a second insulating layer, wherein said second insulating layer is a Group IV metallic oxide.

8. The ultramicroelectrode array of claim 7, wherein said Group IV metallic oxide is Si, Ge, or Sn.

9. The ultramicroelectrode array of claim 8, wherein said Group IV metallic oxide is $SiO_2$.

10. The ultramicroelectrode array of claim 1, further comprising a first metallic adhesion layer below said iridium layer, said first metallic adhesion layer including a transition metal.

11. The ultramicroelectrode array of claim 1, further comprising a first metallic adhesion layer below said iridium layer, said first metallic adhesion layer including a transition metal selected from among Ti, V, Cr, Sc, Nb, Mo, W, or Ta.

12. The ultramicroelectrode array of claim 11, wherein said transition metal is Ti.

13. The ultramicroelectrode array of claim 11, further comprising a second metallic adhesion layer that is a transition metal.

14. The ultramicroelectrode array of claim 13, wherein said transition metal is Ti, V, Cr, Sc, Nb, Mo, W, or Ta.

15. The ultramicroelectrode array of claim 14, wherein said transition metal is Ti.

16. The ultramicroelectrode array of claim 1, wherein the metallic bond pad layer includes Ni, Zn, Pd, Ag, Cd, Pt, Ga, In, or Au.

17. The ultramicroelectrode array of claim 16, wherein said metallic bond pad layer is Au.

18. An ultramicroelectrode sensor device, comprising
   a) a silicon substrate;
   b) a silicon oxide insulating layer on said substrate;
   c) a first titanium adhesion layer on the silicon oxide insulating layer;
   d) an iridium layer deposited over the first titanium adhesion layer;
   e) a gold bond pad layer forming a gold bond pad electrically connected to the iridium layer;
   f) a second titanium adhesion layer on the gold bond pad layer; and
   g) a silicon dioxide insulating layer on the second titanium adhesion layer;
      wherein the iridium layer includes an ultramicroelectrode having an iridium ultramicroelectrode surface exposed through the silicon dioxide insulating layer, the device being configured such that, when used in association with a reference or counter electrode for detecting metal concentration in a fluid, dipping the device in fluid places said exposed iridium ultramicroelectrode surface directly in contact with the fluid whereby a potential applied to the bond pad deposits or strips metal present in the fluid to produce a signal indicative of metal concentration in the fluid.

19. A microelectrode array characterized by having an exposed microelectrode iridium outer surface configured for directly contacting a target fluid and such that, when used in association with a reference or counter electrode for detecting metal concentration in a fluid, application of a potential to the microelectrode iridium outer surface deposits or strips metal at the iridium outer surface to directly measure concentration of trace metal in the target fluid.

* * * * *